US00PP14868P2

(12) United States Plant Patent
White

(10) Patent No.: US PP14,868 P2
(45) Date of Patent: Jun. 8, 2004

(54) EUPHORBIA PLANT NAMED 'BLUE HAZE'

(50) Latin Name: *Euphorbia seguieriana×nicaeensis*
Varietal Denomination: Blue Haze

(76) Inventor: Anthony Robin White, Blackthorn Nursery, Kilmeston, Alresford, Hampshire (GB), SO24 0NL ( * ) Notice: Subject to any disclaimer, the term of this patent is extended or adjusted under 35 U.S.C. 154(b) by 0 days.

(21) Appl. No.: 10/186,078

(22) Filed: Jun. 28, 2002

(51) Int. Cl.[7] ..... A01H 5/00
(52) U.S. Cl. ..... Plt./302
(58) Field of Search ..... Plt./302

*Primary Examiner*—Bruce R. Campell
*Assistant Examiner*—Louanne Krawczewicz Myers

(57) ABSTRACT

A new cultivar of Euphorbia named 'Blue Haze' that is distinguished by a clumping, bushy habit, powder blue foliage and yellow flowers. In combination these traits set 'Blue Haze' apart from all other existing varieties of Euphorbia known to the inventor.

2 Drawing Sheets

Genus: Euphorbia.
Species: *seguieriana×nicaeensis.*
Denomination: Blue Haze.

BACKGROUND OF THE INVENTION

The present invention relates to a new and distinct cultivar of spurge, a hardy perennial that is grown for use as an ornamental container plant or in mixed perennial borders. The new invention is known botanically as Euphorbia and will be referred to hereinafter by the cultivar name 'Blue Haze'.

'Blue Haze' is a hybrid plant that was discovered by the inventor in July 2000 in a cultivated area of Kilmeston, Alresford, England. 'Blue Haze' resulted from the cross between two species of Euphorbia, namely the unnamed female or seed parent *Euphorbia seguieriana* (unpatented) and the unnamed male or pollen parent *Euphorbia nicaeensis* (unpatented). 'Blue Haze' was selected by the inventor for its powder-blue foliage and contrasting yellow-green to soft yellow flowers from mid to late summer. Flowers are held on terminal stems and born axial to the leaf joints with two cyathia cupped by two basally fused floral leaves, also called involucres.

'Blue Haze' performs best in well-drained soil but will tolerate very poor soils. It is hardy to minus 10° Centigrade in heavy soil and hardy to minus 29° Centigrade when planted in well-drained soil. Well-drained compost or ground soil and high light intensity is required for growing.

The closest comparison plant is the species parent *Euphorbia seguieriana* (not patented). 'Blue Haze' is distinguishable from *'Euphorbia seguieriana'* by having red coloration to the stems, broader leaves and yellower flower bracts. The Euphorbia of this group are considered monoecious. In most Euphorbia the stamens mature after the female parts of the flower.

The first asexual reproduction of 'Blue Haze' was accomplished by the inventor using the method of softwood cuttings without bottom heat and was carried out in Kilmeston, Alresford, England in July 2000. Since that time subsequent generations have been determined stable and true to type.

The botanical description of 'Blue Haze' was carried out by observing plants during their second season of growth in Arroyo Grande, Calif. Thus the age of the observed plants ranges from 12 months to 15 months.

SUMMARY OF THE INVENTION

The following traits have been repeatedly observed and represent the distinguishing characteristics of the new Euphorbia cultivar. These traits in combination distinguish 'Blue Haze' from all other existing varieties of Euphorbia. 'Blue Haze' has not been tested under all possible conditions and phenotypic differences may be observed with variations in environmental, climatic, and cultural conditions, however, without any variance in genotype.

1. Euphorbia 'Blue Haze' exhibits a clumping habit.
2. Euphorbia 'Blue Haze' exhibits soft-yellow flowers in summer.
3. Euphorbia 'Blue Haze' exhibits red tinted stems.
4. Euphorbia 'Blue Haze' exhibits powder-blue glaucous foliage with pink tints during cooler temperatures.
5. Euphoribia 'Blue Haze' reaches 46 cm. in height and 61 cm. in width.
6. Euphorbia 'Blue Haze' is hardy to minus 29° Centigrade.

BRIEF DESCRIPTION OF THE DRAWINGS

The accompanying drawings illustrate the distinguishing traits of the new Euphorbia cultivar 'Blue Haze'. The drawings show a plant coming into its second year of growth out-of-doors in a cultivated area of Dorset, England.

The drawing on sheet 1 illustrates the new spring growth of the plant from a side perspective.

The drawing on sheet 2 illustrates the plant in summer bloom from a side perspective. Drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new Euphorbia cultivar 'Blue Haze'. Observations, measurements, values and comparisons were collected in Arroyo Grande Calif. from plants which were 15 months to 18 months old from cuttings, and grown out-of-doors in 14 cm. containers. Color determinations are made in accordance with The 2001 Royal Horticultural Society Colour Chart from London England, except where general color terms of ordinary dictionary significance are used.

Botanical classification: *Euphorbia seguieriana×Euphorbia nicaeensis* 'Blue Haze'.
Species: *Seguieriana×nicaeensis.*
Common name: Spurge.
Parentage: Euphorbia 'Blue Haze' is a hybrid that resulted from the cross between the following parent plants:
*Female parent.*—*Euphorbia seguieriana.*
*Male parent.*—*Euphorbia nicaeensis.*
Propagation method: Softwood cuttings.
Rooting habit: Fibrous.
Time to develop roots: Approximately 21 days at ambient temperature 18–21 Celsius.
Crop time: To fill a four inch container, 1 growing season of approximately 5–8 months from cuttings; to fill a one gallon container, a second growing season, that is approximately 12–15 months from cuttings.
Growth habit: Clumping habit.
Use: Ornamental container plant or landscape plant for mixed perennial borders.
Type: Perennial.
Vigor: Vigorous: achieves dimensions next following within three years.
Height of plant: 46 cm. in height.
Width of plant: 61 cm. in width.
Sexuality: Male.
Cultural requirements: Plant in heavy or well-draining soil and full sunlight.
Diseases and pests: None known to the inventor.
Hardiness: Hardy to minus 29° Centigrade.
Stem:
*Branching habit.*—Clumping.
*Stem colors* (*excluding surface scars on mature stems*).—Young (new growth) stems are 145B. As stem grows, older tissue hardens and darkens through shades of rusty brown, typically in the range 171A to 172A to tints of grey-red 180A. 53D has been observed.
*Stem shape.*—Cylindrical to columnar.
*Stem diameter.*—Stem diameter ranges from 3 mm. to 0.25 cm in diameter.
*Stem length.*—Stem length ranges from 18 to 31 cm. in length.
*Stem surface.*—The surface of new stems is glabrous. Mature stems exhibit bundle scars.
*Shape of bundle scars.*—Linear shaped.
*Dimensions of bundle scars.*—3 mm. in width and 1 mm. in height.
*Color of bundle scars.*—197A.
*Quantity of bundle scars.*—Numerous amounting to approximately 60 in lower half of mature stems.
*Other.*—Stems exude a white milky sap that can be toxic and may elicit dermal irritation.
Foliage:
*Type.*—Evergreen.
*Leaf arrangement.*—Tightly whorled.
*Internode dimensions.*—Ranges from 3 mm. to 0.25 cm. between nodes.
*Leaf division.*—Simple.
*Leaf shape.*—Oblong.
*Leaf length.*—Ranges from 1–3 cm. in length.
*Leaf width.*—Ranges from 2 mm. to 0.25 cm. in width.
*Leaf apex.*—Rounded.
*Leaf venation pattern.*—Parallel.
*Margin.*—Entire.
*Leaf surface* (*abaxial surface*).—Glaucous.
*Leaf surface* (*adaxial surface*).—Glaucous.
*Pubescence.*—Absent.
*Leaf attachment.*—Sessile.
*Mature leaf color* (*adaxial and abaxial surface*).—189A.
*Young leaf color* (*adaxial and abaxial surface*).—191A.
*Seasonal differences.*—Colder temperatures causes the young and mature foliage to become suffused with red tints 53D.
Flower:
*Type.*—Inflorescence.
*Dimensions of inflorescence.*—3.5 cm. in diameter and 2 cm. in height.
*Inflorescence.*—Cyathium.
*Quantity of cyathia per inflorescence.*—Twelve.
*Flowering season.*—Mid to late summer.
*Flower aspect.*—Facing upward.
*Peduncle dimensions.*—9 mm in length and 1.50 mm. in width.
*Peduncle color.*—144A.
*Peduncle surface.*—Glabrous.
*Pedicel dimensions.*—4 mm in length, 0.25 mm in diameter.
*Pedicel color.*—144A.
*Petals.*—Apetalous.
*Sepals.*—Asepalous.
*Involucral bracts.*—Attachment: Connate-perfoliate. Dimensions: 1 cm. in length and 1 cm. in width. Shape: Orbicular. Color: 144A. Number: Two per cyathium.
*Fused or unfused.*—Unfused.
*Margins.*—Entire.
*Flower fragrance.*—Absent.
*Bud shape.*—Ovate.
*Bud dimensions.*—2 mm. in diameter and 4 mm. in length.
*Bud color.*—N144B.
Reproductive organs:
*Stamens.*—One per cyathium.
*Stamen color.*—1C.
*Stamen dimensions.*—3 mm. in length and 1.75 mm. in diameter.
*Anther.*—One in number.
*Anther color.*—144C.
*Anther shape.*—Obcordate.
*Anther dimensions.*—0.50 mm. in width and 0.50 mm. in length.
*Pollen.*—Absent.
*Ovary.*—None observed.
*Pistil.*—None observed.
Seed: No seed has been observed.

I claim:

1. A new and distinct cultivar of Euphorbia plant named 'Blue Haze' as described and illustrated.

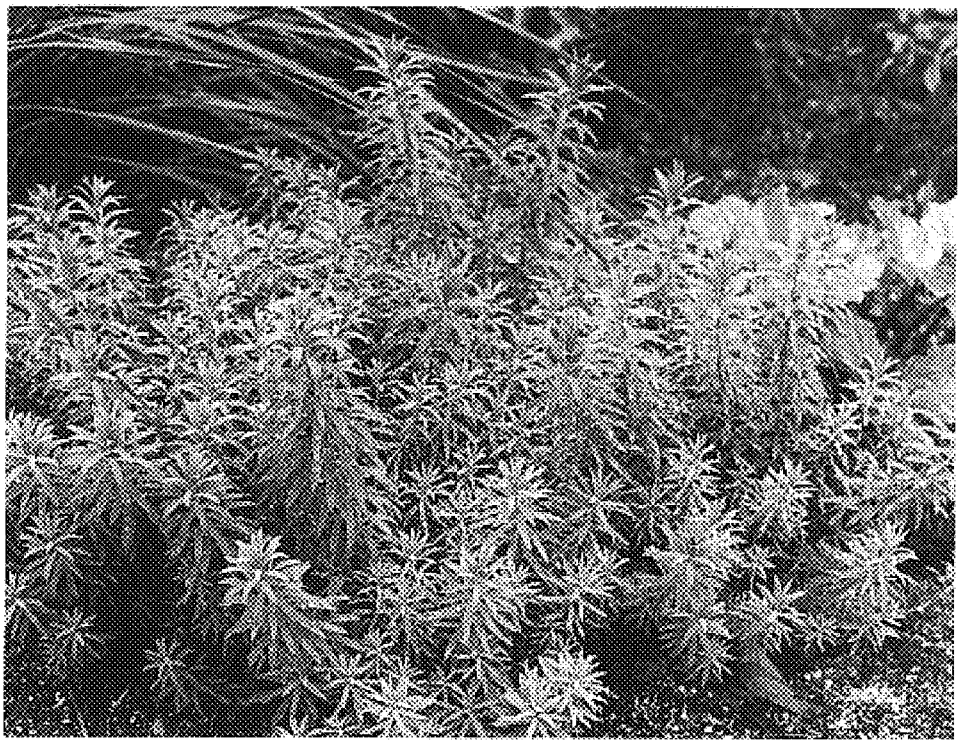

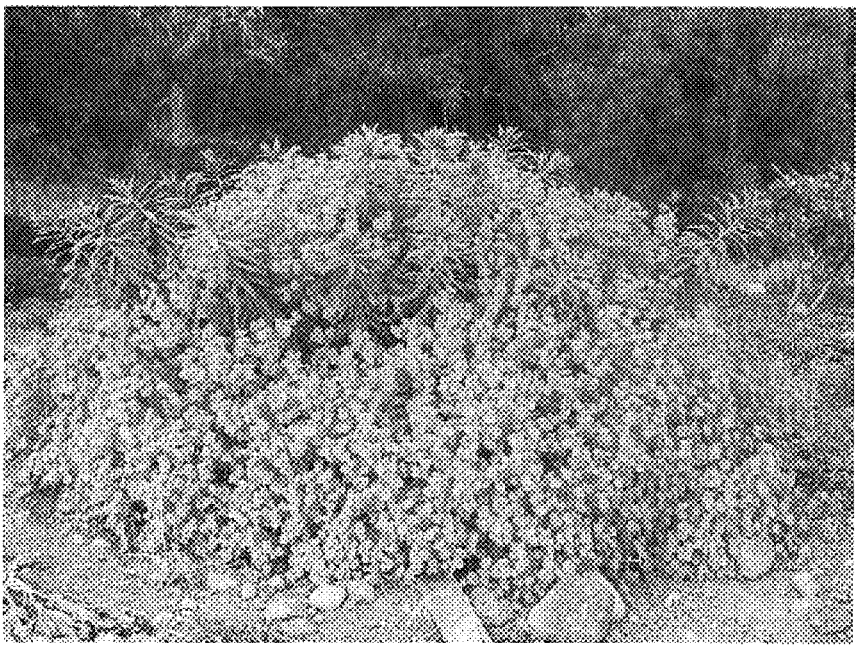

* * * * *